United States Patent [19]
Horan et al.

[11] Patent Number: 5,339,955
[45] Date of Patent: Aug. 23, 1994

[54] INSTRUMENT TRAY WITH INSTRUMENT SUPPORTS

[75] Inventors: Robert Horan, Northridge; A. H. Lynn Valentine, La Granada Hills, both of Calif.

[73] Assignee: Devon Industries, Inc., Chatsworth, Calif.

[21] Appl. No.: 992,616

[22] Filed: Dec. 18, 1992

[51] Int. Cl.⁵ .............................................. B65D 1/36
[52] U.S. Cl. ................................. 206/370; 206/350; 206/364; 206/561; 206/565; 206/571
[58] Field of Search ............................ 206/363–366, 206/368–370, 350, 570–572, 561, 562, 564, 565, 557, 559; 220/626, 632, 636, 771, 575, 556

[56] References Cited

U.S. PATENT DOCUMENTS

| | | | |
|---|---|---|---|
| 435,108 | 8/1890 | Truax | 206/370 |
| 2,659,485 | 11/1953 | Duley et al. | 206/365 |
| 2,766,919 | 10/1956 | Randall | 206/562 X |
| 3,133,635 | 5/1964 | Gordon et al. | 206/366 |
| 3,380,573 | 4/1968 | Gulotta | 206/370 |
| 3,437,423 | 4/1969 | Mondiadis | 206/561 X |
| 3,489,268 | 1/1970 | Mererhoefer | 206/366 |
| 3,601,277 | 8/1971 | Andrews et al. | 206/561 X |
| 3,907,111 | 9/1975 | Levenhager | 206/564 X |
| 4,153,160 | 5/1979 | Leigh | 206/370 |
| 4,195,734 | 4/1980 | Boner et al. | 206/562 X |
| 4,655,360 | 4/1987 | Juhanson | 220/632 X |
| 5,005,590 | 4/1991 | Eldridge, Jr. et al. | 206/363 X |
| 5,024,326 | 6/1991 | Sandel et al. | |
| 5,173,273 | 12/1992 | Brewer | 206/562 X |

OTHER PUBLICATIONS

Brochure "Blade Shield–More Protection for your Surgical Team", Devon Industries, Inc. Nov. 1991.

*Primary Examiner*—Bryon P. Gehman
*Attorney, Agent, or Firm*—Lyon & Lyon

[57] ABSTRACT

A medical instrument tray has a frame of opposing side and end walls having inner and outer panels. Instrument supports extend across the frame and join to inner panels of the side walls. The instrument supports have pegs separated by a central plateau, radiused sections for supporting round instruments, and slots for supporting a flat handle instrument such as scalpel. Finger slots are provided on the bottom side of the tray to allow the tray to be easily carried with the fingers away from the sharp edges or points of the instruments.

9 Claims, 3 Drawing Sheets

INSTRUMENT TRAY WITH INSTRUMENT SUPPORTS

BACKGROUND OF THE INVENTION

The field of the invention is instrument trays and containers.

Various surgical tools and medical instruments are used in surgical procedures. These tools or instruments, many of which have sharp cutting or piercing surfaces, having traditionally been handed back and forth between surgeons and nurses in a operating room. Transferring such instruments hand to hand creates the potential for accidental cutting or stabbing. If the accidental cutting or stabbing occurs with a non-sterile instrument, the potential for infection arises. In addition, if the accidental cutting or stabbing is not immediately noticed, the skin and/or surgical glove barriers can be breached thereby risking infection to the nurse, surgeon, or patient.

SUMMARY OF THE INVENTION

The present invention is directed to a tray for holding and passing or transferring surgical and medical instruments. To this end, an instrument tray has a frame and one or more instrument supports extending across the frame, to hold and support medical instruments. The frame shields cutting or piercing surfaces of the instruments. Finger slots allow the tray to be grasped and handled.

Accordingly, it is an object of the invention to provide a tray for holding and transferring surgical tools and medical instruments. Other and further objects and advantages will appear hereinafter.

BRIEF DESCRIPTION OF THE DRAWINGS

In the drawings, wherein similar reference characters denote similar elements throughout the several views.

DETAILED DESCRIPTION OF THE PREFERRED EMBODIMENT

Figure 1:
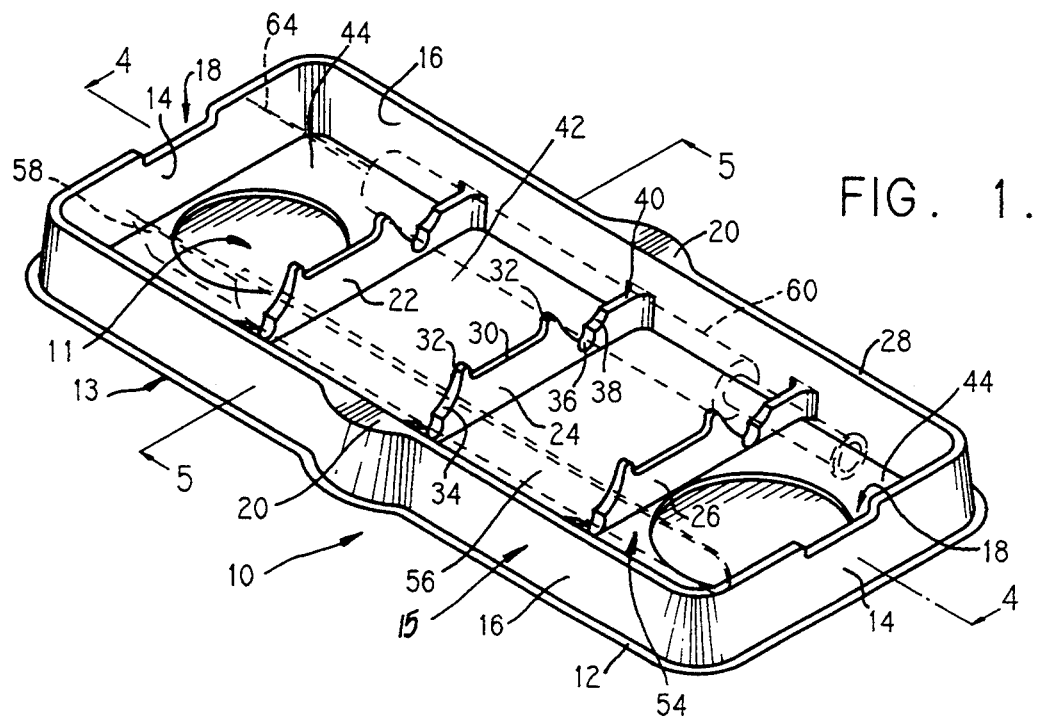
FIG. 1 is a perspective view of the present instrument tray with instruments shown therein in phantom lines.
Figure 4:
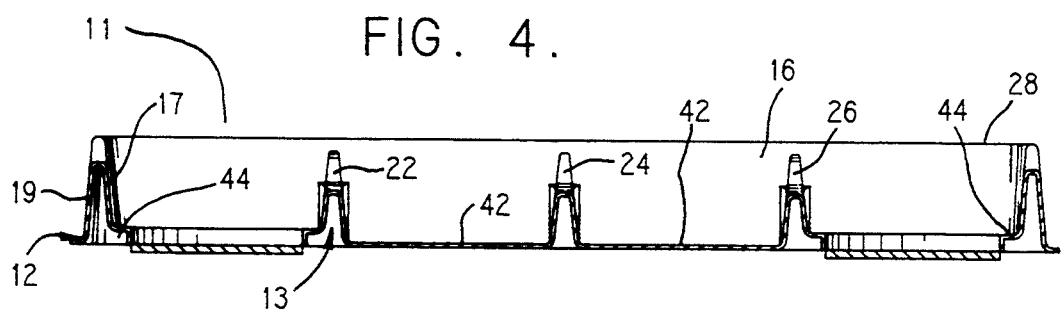
FIG. 4 is a section view taken along line 4—4 of FIG. 1.
Figure 5:
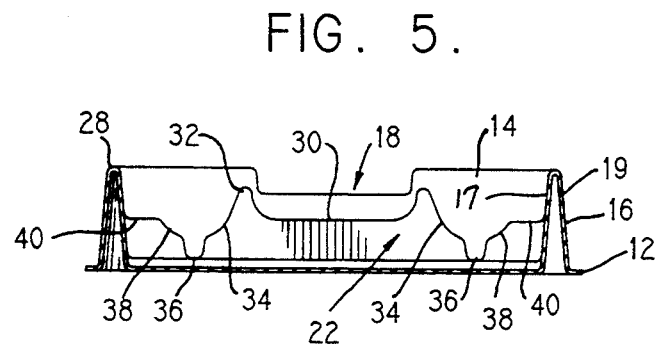
FIG. 5 is a section view taken along line 5—5 of FIG. 1.

Turning into detail to the drawings, as shown in FIGS. 1 and 4, the present tray 10 has a top 11 and bottom 13. The tray 10 is preferably rectangular having longer opposing side walls 16 and shorter end walls 14 which are joined together to form a generally rectangular tray frame 15. A lip 12 extends outwardly from the bottom edge of the tray frame 15. Referring to FIGS. 4 and 5, the side walls 16 and end walls 14 of the tray frame 15 include an outer panel 19 joined to an inner panel 17 at a top rim 28 which may be flat or radiused. Each end wall 14 has an end wall recess 18 to accommodate over length instruments.

Figure 2:
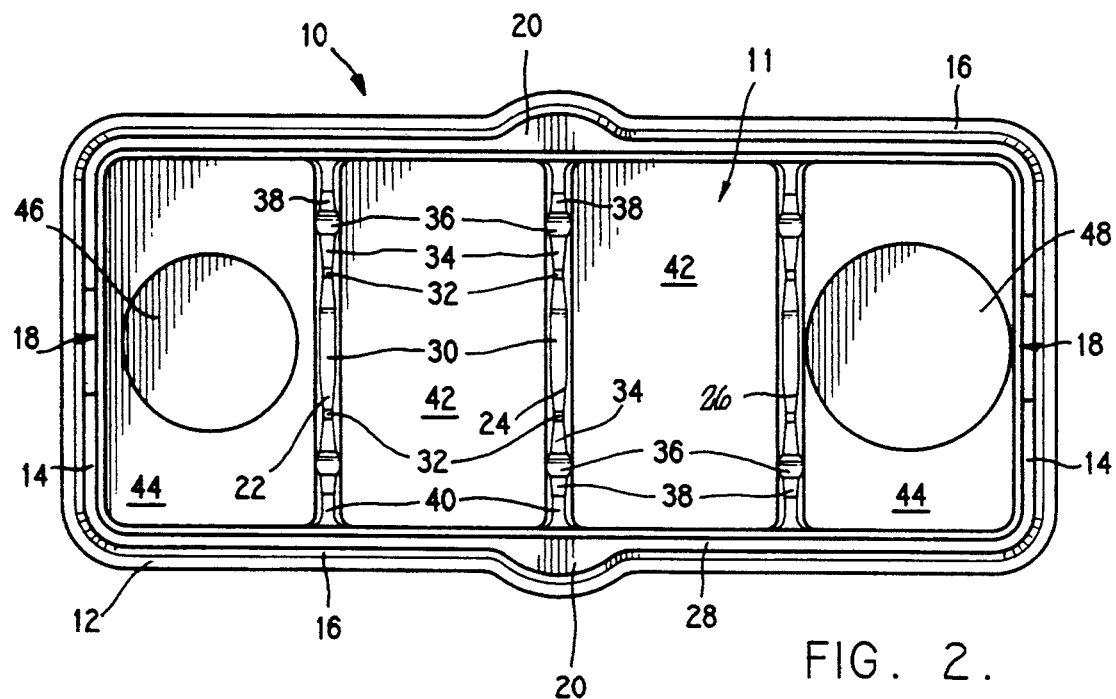
FIG. 2 is a plan view of the tray of FIG. 1.

Referring once again to FIG. 1, in a preferred embodiment, first, second and third instrument supports 22, 24 and 26 are generally equally spaced apart within the tray frame 15. As shown in FIG. 5, each instrument support includes a center plateau 30 in between 2 elevated pegs 32. An inner radius section 34 slopes downwardly and outwardly from each peg 32 to a slot 36. An outer radiused section 38 slopes upwardly from the slot 36 to a side ledge 40 which joins the inner panel 17 of the frame side walls 16. As shown in FIGS. 1 and 4, flat center floors 42 extend between and join with the instrument supports and side walls 16. End floors 44 similarly extend between and join with the first and third instrument supports 22 and 26, and the inner panels 17 of the end walls 14 and side walls 16. As shown in FIGS. 2 and 4, a first round depression 46 and a second larger round depression 48 are provided in the end floors 44. The first round depression 46 is dimensioned to hold a two-ounce med cup, while the larger round depression 48 is dimensioned to hold a four-ounce med cup.

Figure 3:
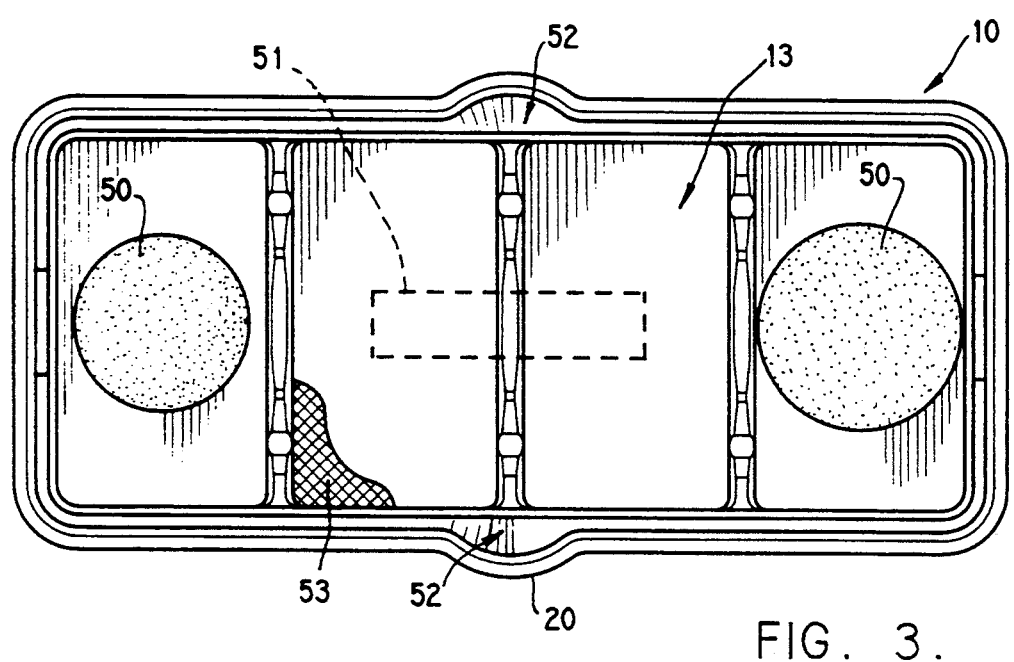
FIG. 3 is a bottom view of the present tray showing alternate preferred embodiments.

Referring to FIG. 3, round metal plates 50 are advantageously bonded onto the bottom surface of the tray 10, on the first and second round depressions 46 and 48 so that the tray can be held onto a magnetic drape commonly used in surgery. Alternatively, a single magnetic metal strip 51 may be provided spanning the underside of the center floors 42. For use with cloth drapes, a high friction, non-skid material may be applied to the bottom of the tray.

Referring still to FIG. 3, preferably, the tray 10 includes finger slots 52 centrally located in the tray frame 15. To provide a convenient grasping surface, the outer panels 19 of the side walls 16 bow outwardly at the center of the tray 10. The tray may be easily grasped and carried by inserting a thumb and one or more fingers into the opposing finger slots 52 at the bottom 13 of the tray. As the finger slots 52 are generally aligned with the second instrument support 24, the tray, even if made of thin material, has relatively high compression strength across the finger slots 52, allowing the tray 10 to be grasped firmly without deforming it.

Referring once again to FIG. 1, as shown in phantom line, a scalpel 54 has a handle 56 and a blade 58. The slots 36 in the instrument supports 22, 24 and 26 are dimensioned to accommodate and secure the handle 56 of the scalpel 54. Accordingly, the scalpel 54 can be securely placed and held in the tray 10 by relatively gently pressing the handle 56 into the slots 36. Also as shown in FIG. 1, a needle and syringe combination is held by the tray 10 with the syringe 60 resting on the inner and outer radiused sections 34 and 38 of the instrument supports. The needle 64 and the scalpel blade 58 are shielded by the frame to protect against accidental stabbing or cutting. The slots 36 and radius sections 34 and 38 are dimensioned to accommodate the largest commonly used scalpel handle and syringe, respectively. Smaller sizes placed in the tray are held less tightly.

Figure 6:
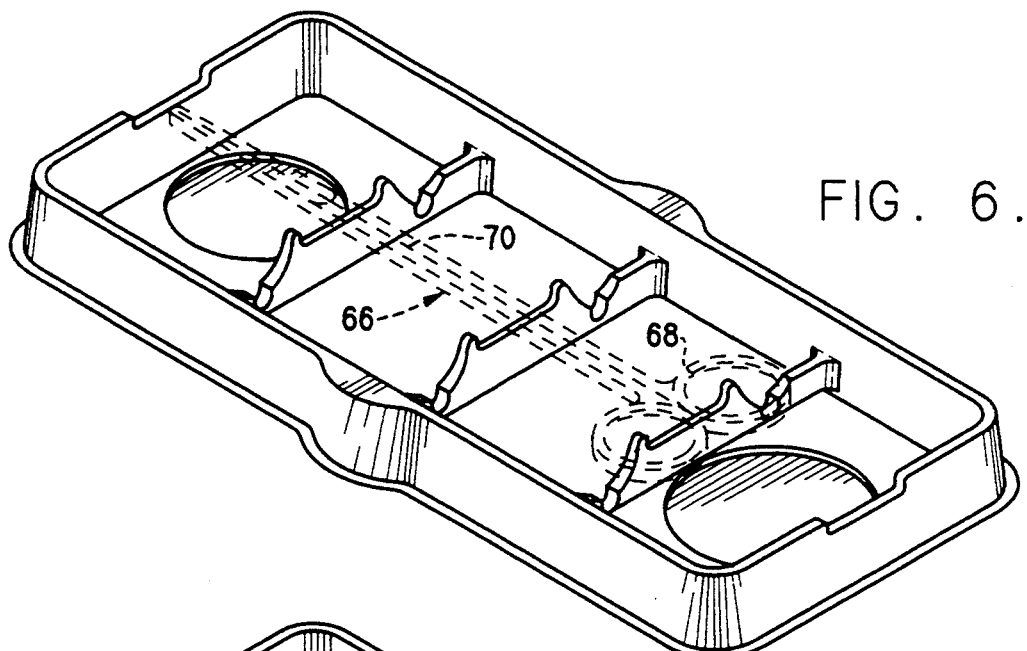
FIG. 6 is a perspective view of the present tray holding an instrument having ring handles.
Figure 7:
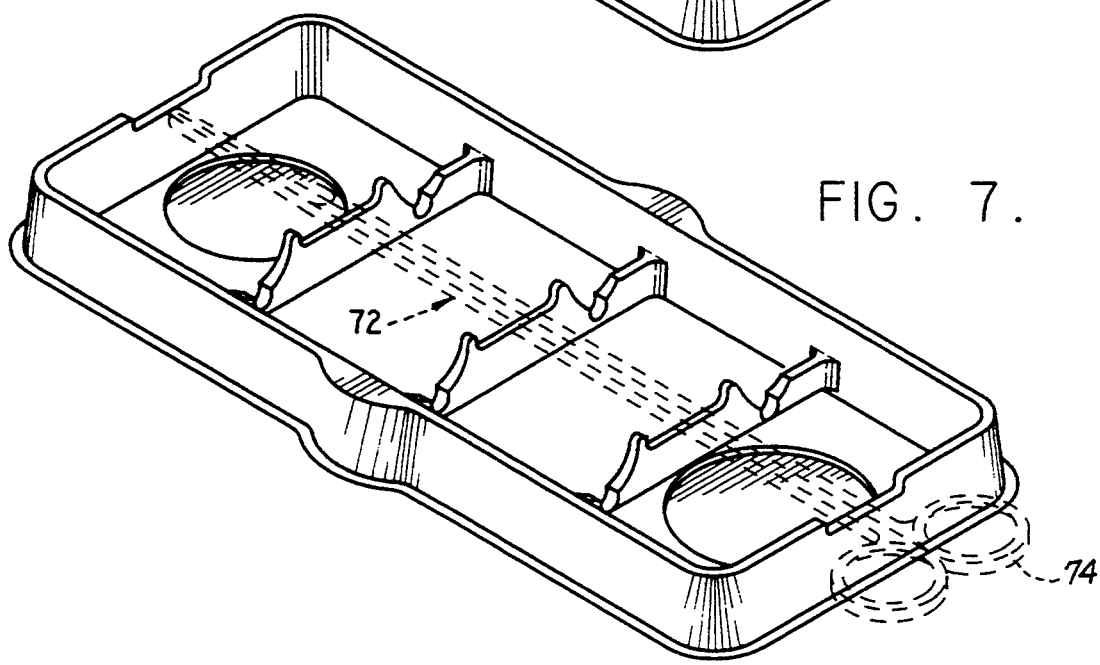
FIG. 7 is a perspective view of the present tray holding a longer instrument with ring handles.

Referring to FIG. 6, instruments having ring handles, such as a forcep 66, scissors, clamp, etc. can be carried in the tray 10 with the pegs 32 extending into the ring handles 68 of the instrument 66, and with the body 70 of the instrument resting on the center plateau 30 of the instrument supports 22, 24 and 26. As shown in FIG. 7, for an over length ring handle instrument 72, the handle 74 extends through the end walls recess 18 with the body of the instrument supported within the tray frame 15 on the center plateaus 30 of the instrument supports.

Preferably, the tray is manufactured as a thin wall integral plastic molded rectangular unit, is approximately 9 inches long, and includes three instrument supports. However, obviously, other sizes, shapes, materials and number of instrument supports are possible.

Thus, a novel instrument tray is disclosed. While embodiments and applications of this invention have been shown and described, it would be apparent to those skilled in the art that many more modifications are possible without departing from the inventive concepts herein. The invention, therefore, is not be restricted except in the spirit of the appended claims.

What is claimed is:

1. A tray for handling medical instruments comprising:
    a rectangular frame having inner and outer frame walls joined at a top frame rim, the frame including opposing sides and ends;
    a plurality of instrument supports extending laterally across the frame and adjoining the inner frame walls at the opposing sides, each instrument support including:
        a pair of pegs spaced apart by a generally flat central rib;
        an inner radius section adjoining each peg; and
        an outer radius section spaced apart from the inner radius section by a slot;
    a frame floor adjoining the instrument supports and the inner frame walls; and
    a pair of finger slots in the opposing sides in between the inner and outer frame walls for grasping the tray.

2. The tray of claim 1 further comprising a non-skid material attached to a bottom surface of the floor.

3. The tray of claim 1 further comprising a magnetically attracted plate attached to a bottom surface of the tray.

4. The tray of claim 1 further comprising a recess in at least one of the frame ends.

5. The tray of claim 1 wherein the tray is a single molded plastic unit.

6. The tray of claim 1 further comprising a lip attached to the outer frame walls along a bottom edge of the frame.

7. The tray of claim 1 further comprising a side ledge on each instrument support, between the outer radius section and the inner frame walls.

8. The tray of claim 1 further comprising a recess approximately centered in each of the opposing ends, the recess extending from the top frame rim towards the floor, to allow a handle of an overlength instrument supported on the instrument supports to extend beyond one of the opposing sides.

9. A medical instrument tray comprising:
    a generally rectangular frame having an inner frame wall and an outer frame wall joined at a top frame rim, the frame including a first side and a second side and a first end and a second end;
    a plurality of instrument supports extending laterally across the frame, each instrument support comprising:
        a first ledge joined to the inner frame wall at the first side;
        a first slot extending through a first radius section;
        a first peg joined to the first radius section;
        a generally flat central plateau joined to the first peg;
        a second peg joined to the central plateau and spaced apart from the first peg;
        a second radius section joined to the second peg;
        a second slot extending through the second radius section;
        a second ledge joined to the second radius section and to the inner frame wall at the second side;
    a frame floor joined to the instrument supports and the inner frame walls; and
    finger slots in the first side and the second side in between the inner and outer frame walls, for grasping the underside of the tray.

* * * * *